US006194457B1

(12) United States Patent
Braswell et al.

(10) Patent No.: US 6,194,457 B1
(45) Date of Patent: *Feb. 27, 2001

(54) LIQUID EYE DROP COMPOSITION

(76) Inventors: A. Glenn Braswell, 520 Washington Blvd. Suite 420, Marine dél Rey, GA (US) 90292; Kenneth J. Absher, 377 S. Nevada St., Carson City, NV (US) 89703; Alex Duarte, 10304 Banner Lava Cap Rd., Nevada City, CA (US) 95959

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,755

(22) Filed: Jan. 29, 1998

Related U.S. Application Data

(60) Provisional application No. 60/036,516, filed on Jan. 29, 1997.

(51) Int. Cl.[7] ................................................. A61K 31/225
(52) U.S. Cl. .......................... 514/547; 514/561; 514/562; 514/912
(58) Field of Search .................................. 514/547, 561, 514/562, 912

(56) References Cited

U.S. PATENT DOCUMENTS

| 5,075,116 | 12/1991 | LaHaye et al. . |
| 5,156,852 | * 10/1992 | La Haye et al. ..................... 424/617 |

OTHER PUBLICATIONS

Derwent Abstract, C94–159890. Abecassis et al. 1994.*
"Scientific Basis for Medical Therapy of Cataracts by Antioxidants", Shambhu D. Varma, Am J Clin Nutr., pp. 335S–345S, 1991.
"Glutathione Levels of the Human Crystalline Lens in Aging and its Antioxidant Effect Against the Oxidation of Lens Proteins", Akira Kamei, Biol. Pharm. Bull., vol. 16, No. 9, pp. 870–875, 1993.
"Glutathione and Ageing: Ideas and Evidence", Robert H. Fletcher and Suzanne W. Fletcher, The Lancet, vol. 344, pp. 1379–1380, Nov. 19, 1994.
"Antioxidant Status in Persons With and Without Senile Cataract", Paul F. Jacques et al., Arch Ophthalmol, vol. 106, pp. 337–340, Mar. 1988.
"Vitamin E Intake and Risk of Cataracts in Humans", James McD. Robertson et al., Annals New York Academy of Sciences, pp. 372–382, (1993).
"Prevention of Selenite Cataract by Vitamin C", P. S. Devamanoharan et al., Exp. Eye Res., vol. 52, pp. 563–568, 1991.
"Epidemiologic Evidence of a Role for the Antioxidant Vitamins and Carotenoids in Cataract Prevention", Paul F. Jacques et al., Am J Clin Nutr, pp. 352S–355S, 1991.
"Endogenous Ascorbate Regenerates Vitamin E in the Retina Directly and in Combination with Exogenous Dihydrolipoic Acid", Detcho A. Stoyanovsky et al., Current Eye Research, pp. 181–189, 1994.
"The Redox Couple Between Glutathione and Ascorbic Acid: A Chemical and Physiological Perspective", Barry S. Winkler et al., Free Radical Biology & Medicine, vol. 17, No. 4, pp. 333–349, 1994.
"Histochemical Localization of Zinc and Copper in Rat Ocular Tissues", Yoshiaki Hirayama, Acta Histochem. vol. 89. pp. 107–111, 1990.
"Zinc Uptake by Primate Retinal Pigment Epithelium and Choroid", David A. Newsome et al., Current Eye Research, vol. 11, No. 3, pp. 213–217, 1992.
"Cataract Breakthrough, The Booklet", Dr. Alex Duarte, pp. 1–44, (No Date).
"X–Ray Microanalysis of Ocular Melanin in Pigs Maintained on Normal and Low Zinc Diets", Don A. Samuelson et al., Exp. Eye Res., vol. 56, pp. 63–70, 1993.
"Vitamin E Inhibits Retinal Pigment Epithelium Cell Proliferation in Vitro", Daniel Mojon et al., Ophthalmic Res., vol. 26, pp. 304–309, 1994.
"The Premature Infant, Vitamin E Deficiency and Retrolental Fibroplasia", Lois Johnson, M.D. et al., The American Journal of Clinical Nutrition, vol. 27, pp. 1158–1173, Oct. 1974.
"Retrolental Fibroplasia: Efficacy of Vitamin E in a Double–Blind Clinical Study of Preterm Infants", Helen Mintz Hittner, M.D., et al., The New England Journal of Medicine, vol. 305, No. 23, pp. 1365–1371, Dec. 3, 1981.
Are Antioxidants or Supplements Protective for Age–Related Macular Degeneration?, Sheila West, PhD., et al., Arch Ophthalmol, vol. 112, pp. 222–227, Feb. 1994.
"Mercapturic Acid Pathway Enzymes in Bovine Ocular Lens, Cornea, Retina and Retinal Pigmented Epithelium", Russell P. Saneto et al., Exp. Eye Res., pp. 107–111, 1982.
"Glutathione Levels in Human Cataract", G. Greco et al., pp. 1019–1020.
"Serum Antioxidant Vitamins and Risk of Contract", Paul Knekt et al., BMJ, Vol. 305, pp.1392–1394, Dec. 5, 1992.
"Plasma Antioxidants and Risk of Cortical and Nuclear Cataract", Susan Vitale et al., Epidemiology, Vol. 4, No. 3, pp. 195–203, May 1993.
"Dietary Carotenoids, Vitamin A, C, and Advanced Age–Related Macular Degeneration", Johanna M. Seddon, MD., JAMA, Vol. 272, No. 18, pp. 1413–1420, Nov. 9, 1994.
"Protective Role of Vitamin E in Cataract Development", VERIS Vitamins E Research & Information Service, 4 pp. Feb. 1990.
"A Possible Role for Vitamins C and E in Cataract Prevention", James McD Robertson et al., Am J Clin Nutr., Vol. 53, pp. 346S–351S, 1991.

* cited by examiner

*Primary Examiner*—Zohreh Fay
(74) *Attorney, Agent, or Firm*—McKenna & Cuneo, L.L.P.

(57) ABSTRACT

A composition that is used as an eye treatment contains reduced glutathione, vitamin A and vitamin E, as well as one or more of zinc sulfate, boric acid and potassium as buffering agents. The composition also may contain a lubricant and a preservative. The composition is a sterile isotonic solution. The composition is used in a method of treating eyes for the alleviation of irritations and/or dryness, as well as for the prevention and treatment of cataracts.

20 Claims, No Drawings

LIQUID EYE DROP COMPOSITION

This nonprovisional application claims the benefit of U.S. Provisional Application No. 06/036,516, filed Jan. 29, 1997.

BACKGROUND OF THE INVENTION

1. Field of the Invention

This invention relates to a liquid composition for treatment of the eyes. The liquid eye drop composition may-be used to treat irritations of the eye, dryness of the eye, and/or the onset or progression of cataracts.

2. Discussion of Related Art

The ocular lens of the eye is a relatively pliable and normally transparent tissue held in suspension between the aqueous and vitreous humors. The tissue has a fibrous type structure. The lens functions as a converging lens, in conjunction with the cornea, pupil, aqueous humor and vitreous humor. The pliability and transparency of the lens are necessary for the proper functioning of the lens in image formation and visual perception.

The lens of the eye is constantly exposed to light and ambient oxygen, and is thus very susceptible to oxidation, particularly light-induced lipid peroxidation. The lens has a complex biochemical system, well understood in the art, relying upon proteins, particularly proteins containing sulfhydryl groups, to maintain the system and in turn the transparency of the lens.

Light entering the eye permits the generation of free radicals within the lens, in particular the superoxide radical $O_2^-$, which in turn can degenerate into other free radicals such as hydrogen peroxide and hydroxide radicals. These free radicals act to oxidize the proteins of the lens. Oxidation of the proteins is known to be a major factor leading to the onset of cataracts, which is a loss of transparency of the lens. See, for example, Varma, "Scientific Basis for Medical Therapy of Cataracts by Antioxidants", Am. S. Clin. Nutr., vol. 53, pps. 335S–345S (1991).

Accordingly, the lens of the eye has an antioxidant defense system to respond to an oxidative stress and maintain the integrity of the lens. Various studies have shown that the antioxidant defense system includes the enzymes glutathione peroxidase, catalase and superoxide dismutase, and the antioxidants vitamin A (ascorbic acid), vitamin E ($\alpha$-tocopherol) and $\beta$-carotene. See, for example, Kamei, "Glutathione Levels of the Human Crystalline Lens in Aging", Biol. Pharm. Bull., vol. 16, no. 9, pps. 870–875 (1993); Fletcher et al., "Glutathione and Aging: Ideas and Evidence", The Lancet, vol. 344, pps. 1379–1380 (1994); and Jacques et al., "Antioxidant Status in Persons With and Without Senile Cataracts", Arch. Opthalmol., vol. 106, pps. 337–340 (1988).

The role of each of the above materials in protecting the lens against degradation by oxidation has also been widely studied. Most studies have focused upon dietary supplementation of the materials to preserve the antioxidant defense system of the lens during aging, thus preventing or slowing the onset of cataracts. See, for example, Robertson et al., "Vitamin E Intake and Risk of Cataracts in Humans", Annals New York Academy of Sciences, pps. 372–382; "Protective Role of Vitamin E in Cataract Development", Vitamin E Research Information Service (1990); Devamanoharan et al., "Prevention of Selenite Cataract by Vitamin C", Exp. Eye Res., vol. 52, pps. 563–568 (1991); and Jacques et al., "Epidemiologic Evidence of a Role for the Antioxidant Vitamins and Cartenoids in Cataract Prevention", Am. J. Clin. Nutr., vol. 53, pps. 352S–355S (1991). See also U.S. Pat. No. 5,075,116 to LaHaye et al.

Studies have also confirmed that the materials vitamin A, vitamin E and glutathione have a close interaction in regenerating one another following oxidation of one or more of these molecules. See, for example, Stoyanovsky et al., "Endogenous Ascorbate Regenerates Vitamin E in the Retina Directly and in Combination With Exogenous Dihydrolipoic Acid", Current Eye Research (1994); and Winkler et al., "The Redox Couple Between Glutathione and Ascorbic Acid: A Chemical and Physiological Perspective", Free Radical Biology & Medicine, vol. 17, no. 4, pps. 333–349 (1994).

A role has also been reported for zinc and copper in maintenance of retinal metabolism. See Hirayama, "Histochemical Localization of Zinc and Copper in Rat Ocular Tissues", Acta Histochem., vol. 89, pps. 107–111 (1990). Zinc has been cited as a cofactor for several antioxidant systems present in the retinal pigment epithelium. See Newsome et al., "Zinc Uptake by Primate Retinal Pigment Epithelium and Choroid", Current Eye Research, vol. 11, no. 3, pps. 213–217 (1992).

Although extensive reporting has been done on the significance of dietary supplementation of various lens antioxidant system materials in maintaining the integrity of the defense system in times of oxidative stress and throughout aging, there is little discussion related to eye drop formulations that combat oxidation in the lens. One exception is Cataract Breakthrough, The Booklet, by Dr. Alex Duarte, discussing research in which the three amino acids cysteine, glycine and glutamic acid, the amino acids that make up and synthesize glutathione, were introduced to the lens through eye drops. Dr. Duarte recommends a cataract prevention treatment involving these eye drops in conjunction with dietary supplementation of all antioxidant defense materials.

SUMMARY OF THE INVENTION

It is an object of the present invention to develop a liquid eye treatment composition, that is an eye drop composition, that may be used in combating oxidation within the lens of the eye. It is a further object of the invention to develop an eye drop composition that may further be used to relieve irritations from the eye and eliminate dryness of the eye.

These and other objects are achieved with a liquid eye treatment composition containing a specific combination of lens antioxidant defense materials and buffering agents. The eye drop composition, when added to the eye, not only is capable of alleviating irritations and/or dryness, but is also capable of preventing the onset of cataracts from aging, or delaying or halting the progression of cataracts in patients already having cataracts. The composition of the invention achieves such results without the need for dietary supplementation of other antioxidant materials.

DETAILED DESCRIPTION OF PREFERRED EMBODIMENTS

The eye treatment composition of the invention must contain each of the antioxidant materials vitamin A, vitamin E and reduced glutathione.

By "reduced glutathione" is meant a mixture of the three amino acids glutamic acid, cysteine and glycine which comprise and synthesize glutathione. The reduced glutathione preferably comprises these amino acids in substantially equimolar amounts, although glutamic acid and glycine may be included in greater amounts to account for reported lower percentage penetrations of these amino acids through the cornea compared to cysteine. Once within the fibrous structure of the lens, these amino acids interact to synthesize glutathione, which is known to act as an antioxidant in the lens.

The amount of reduced glutathione in the composition is from, for example, 0.1 to 10% by weight, preferably from 0.5 to 5% by weight, more preferably from about 1 to about 3% by weight of the composition. The amount of vitamin A in the composition is from, for example, 0.01 to 5% by weight, preferably from 0.05 to 2% by weight, more preferably less than about 0.1% by weight of the composition. The amount of vitamin E in the composition is from, for example, 0.01 to 10% by weight, preferably from 0.05 to 5% by weight, more preferably from about 0.1 to about 1% by weight of the composition.

As discussed above, each of the antioxidant materials cooperate with one another in the lens antioxidant defense system. The cooperation enables cyclical regeneration of the antioxidants, avoiding rapid elimination of the antioxidants from the eye which would require continues replenishment (that is, continuous eye drop application) if such were to occur.

The eye drop composition of the invention also preferably includes buffering agents to adjust the acidity or alkalinity of the composition. In order for the eye drop composition to be accepted by the eye without causing irritation, it is important that the composition be an isotonic solution in that it have the same or similar pH to mammalian eye fluids. Typically, this requires that the pH of the composition be between 6.1 to 6.3.

The buffering agents preferably include one or more of zinc sulfate, boric acid and potassium, for example potassium bicarbonate. Other known buffering agents may also be included. In a most preferred embodiment, the buffering agents comprise all three of zinc sulfate, boric acid and potassium.

The amount of each buffering agent is that amount necessary to be effective in achieving a pH of the composition of from 6.1 to 6.3. Typically, the total amount of buffering agents present in the composition ranges from 1 to 15% by weight, preferably from 2 to 10% by weight of the composition. When zinc sulfate, boric acid and potassium are all present in the composition, the amount of zinc sulfate is from, for example, 0.01 to 5% by weight, preferably from 0.05 to 2% by weight, more preferably from about 0.05 to about 1% by weight of the composition, the amount of boric acid is from, for example, 0.1 to 10% by weight, preferably from 0.5 to 5% by weight, more preferably from about 1 to about 3% by weight of the composition, and the amount of potassium, preferably potassium bicarbonate, is from, for example, 0.1 to 10% by weight, preferably from 0.5 to 5% by weight, more preferably from about 0.5% to about 2% by weight of the composition of the composition.

An additional benefit of including zinc sulfate as a buffering agent is the materials role as a cofactor in antioxidant systems. An additional benefit from including potassium as a buffering agent is the need for the lens to uptake this material while expelling sodium. Thus, potassium may assist in the expulsion of sodium from the lens and eye, thereby reducing dryness and irritation of the eye.

The eye drop composition also preferably includes a lubricant. Any known, suitable eye drop composition lubricants may be used, for example cellulose derivatives. A preferred lubricant in the composition is sodium carboxymethyl cellulose because of its lubricating ability and inertness towards the antioxidant materials of the composition. When present, the lubricant is contained in the composition in an amount of from, for example, 0.01 to 5% by weight, preferably from 0.05 to 2% by weight, more preferably from about 0.1 to about 1% by weight of the composition.

The composition also may preferably include a preservative. Any known preservatives conventionally used in eye drop compositions are suitable. For example, the preservative may be benzalkonium chloride and other quaternary ammonium preservative agents, phenylmercuric salts, sorbic acid, chlorobutanol, disodium edetate, thimerosal, methyl and propyl paraben, benzyl alcohol, and phenyl ethanol. Purified benzyl alcohol is preferred. When present, the preservative is contained in the composition in an amount of from, for example, 0.1 to 5% by weight, preferably from 0.5 to 3% by weight, more preferably less than about 1.5% by weight of the composition.

The eye treatment composition of the invention is a solution preferably having a vehicle of water, preferably deionized water, or mixtures of water and water-miscible solvents such as, for example, lower alkanols or arylalkanols, phosphate buffer vehicle systems, isotonic vehicles such as boric acid, sodium chloride, sodium citrate, sodium acetate and the like, vegetable oils, polyalkylene glycols, and petroleum based jelly, as well as aqueous solutions containing ethyl cellulose, carboxymethyl cellulose and derivatives thereof, hydroxypropylmethyl cellulose, hydroxyethyl cellulose, carbopol, polyvinyl alcohol, polyvinyl pyrrolidone, isopropyl myristate and other conventionally-employed non-toxic, pharmaceutically acceptable organic and inorganic carriers. The aqueous-based vehicle comprises the balance of the eye drop composition.

Preferably, the composition is in the form of an isotonic solution. Because the composition is applied to the eye, the composition should be sterile.

The composition may also contain non-toxic auxiliary substances such as emulsifying agents, wetting agents, bodying agents and the like such as, for example, polyethylene glycols, carbowaxes, and polysorbate 80. Other conventional ingredients can be employed such as sorbitan monolaurate, triethanolamnine, oleate, polyoxyethylene sorbitan 35 monopalmitylate, dioctyl sodium sulfosuccinate, monothioglycerol, thiosorbitol, ethylenediamine tetraacetic acid, and the like.

In treating irritations and/or dryness of the eye, and/or in treating cataracts, the eye drop composition is preferably added to the eye in an amount of from, for example, 1 to 8 drops per day, most preferably from 1 to 3 drops per day. The applications are preferably spread out evenly over the course of a day so that the applications occur from, for example, 1 to 4 times per day.

The composition may be used as either or both a common eye drop and a specific drug in the treatment of cataracts. If used prior to the onset of cataracts, the composition assists in preserving the integrity of the lens antioxidant defense system in order to prevent, or at least greatly delay, the onset of cataracts, particularly cataracts from aging. If used after cataracts are detected, the composition acts to restore the antioxidant defense system and thereby prevent or greatly slow further progression of cataracts.

EXAMPLE

The following eye drop formulation is prepared in accordance with the invention. The eye drop formulation has a total of 2 milliliters of formula.

| | |
|---|---|
| Reduced glutathione | 2% by weight |
| Boric acid | 2% by weight |
| Potassium bicarbonate | <2% by weight |
| Zinc sulfate | <0.1% by weight |
| Carboxymethyl cellulose | <0.2% by weight |
| Vitamin A | <0.1% by weight |
| Vitamin E | <1% by weight |
| Benzyl alcohol | <1% by weight |
| Distilled water | balance |

The formula is formed by mixing the reduced glutathione, boric acid, benzyl alcohol, potassium bicarbonate and zinc sulfate in a minor amount of the water, for example about 1% or less of the total water in the end formula. The mixture is then filtered. The filtered mixture is added to a mixture of carboxymethyl cellulose, vitamin A, vitamin E and the balance of the water.

The invention has been described in detail with particular reference to preferred embodiments thereof. However, it will be appreciated that those skilled in the art, upon consideration of this disclosure, may make variations and modifications within the spirit and scope of the invention.

What is claimed is:

1. A liquid eye composition comprising an isotonic solution of reduced glutathione, vitamin A, vitamin E, and one or more buffering agents, said buffering agents producing a pH in said composition similar to mammalian eye fluids, wherein said reduced glutathione comprises glutamic acid, cysteine and glycine.

2. The composition according to claim 1, wherein the reduced glutathione comprises substantially equimolar amounts of glutamic acid, cysteine and glycine.

3. The composition according to claim 1, wherein the reduced glutathione is present in an amount of from 0.1 to 10% by weight of the composition.

4. The composition according to claim 1, wherein the vitamin A is present in an amount of from 0.01 to 5% by weight of the composition.

5. The composition according to claim 1, wherein the vitamin E is present in an amount of from 0.01 to 10% by weight of the composition.

6. The composition according to claim 1, wherein the buffering agents are present in an amount of from 1 to 15% by weight of the composition.

7. The composition according to claim 1, wherein the buffering agents are a mixture of zinc sulfate, boric acid and potassium.

8. The composition according to claim 1, wherein the composition further comprises a lubricant.

9. The composition according to claim 8, wherein the lubricant is sodium carboxymethylcellulose.

10. The composition according to claim 1, wherein the composition further comprises a preservative.

11. The composition according to claim 10, wherein the preservative is purified benzyl alcohol.

12. A method of preventing or reducing the onset or progression of cataracts, comprising applying to an eye a liquid eye drop composition comprising an isotonic solution of reduced glutathione, vitamin A, vitamin E, and one or more buffering agents, said buffering agents producing a pH in said composition similar to mammalina eye fluids, wherein said reduced glutathione comprises glutamic acid, cystein and glycine.

13. The method according to claim 12, wherein the reduced glutathione comprises substantially equimolar amounts of glutamic acid, cysteine and glycine.

14. The method according to claim 12, wherein the reduced glutathione is present in an amount of from 0.1 to 10% by weight of the composition.

15. The method according to claim 12, wherein the vitamin A is present in an amount of from 0.01 to 5% by weight of the composition.

16. The method according to claim 12, wherein the vitamin E is present in an amount of from 0.01 to 10% by weight of the composition.

17. The method according to claim 12, wherein the composition further comprises a lubricant.

18. The method according to claim 12, wherein the composition further comprises a preservative.

19. The method according to claim 12, wherein the application is 1 to 8 drops to the eye per day.

20. The method according to claim 19, wherein the drops are applied at intervals of 1 to 4 times per day.

* * * * *

UNITED STATES PATENT AND TRADEMARK OFFICE
CERTIFICATE OF CORRECTION

PATENT NO. : 6,194,457 B1
DATED : February 27, 2001
INVENTOR(S) : Braswell, et al.

It is certified that error appears in the above-identified patent and that said Letters Patent is hereby corrected as shown below:

Column 6,
Line 20, "mammalina" should read -- mammalian --

Signed and Sealed this

Sixth Day of November, 2001

Attest:

*Nicholas P. Godici*

NICHOLAS P. GODICI
*Attesting Officer*   *Acting Director of the United States Patent and Trademark Office*